United States Patent [19]

Blank et al.

[11] Patent Number: 4,946,684

[45] Date of Patent: Aug. 7, 1990

[54] FAST DISSOLVING DOSAGE FORMS

[75] Inventors: Robert G. Blank; Dhiraj S. Mody, both of Hammonton; Richard J. Kenny, Manahawkin; Martha C. Aveson, Voorhees, all of N.J.

[73] Assignee: American Home Products Corporation, New York, N.Y.

[21] Appl. No.: 368,612

[22] Filed: Jun. 20, 1989

[51] Int. Cl.[5] .......... A61K 9/34

[52] U.S. Cl. .......... 424/441; 424/485; 424/488

[58] Field of Search .......... 424/485, 440, 488, 441

[56] References Cited

U.S. PATENT DOCUMENTS

| | | | |
|---|---|---|---|
| 4,371,516 | 2/1983 | Gregory et al. | 424/485 |
| 4,695,463 | 9/1987 | Yang et al. | 424/488 |
| 4,698,264 | 10/1987 | Steinke | 424/488 |
| 4,760,093 | 7/1988 | Blank et al. | 514/629 |
| 4,760,094 | 7/1988 | Blank et al. | 514/629 |
| 4,767,789 | 8/1988 | Blank et al. | 514/629 |
| 4,771,077 | 9/1988 | Reuter et al. | 514/629 |
| 4,803,081 | 2/1989 | Falk et al. | 424/488 |
| 4,835,186 | 5/1989 | Reuter et al. | 514/570 |
| 4,835,187 | 5/1989 | Reuter et al. | 514/570 |
| 4,835,188 | 5/1989 | Ho et al. | 514/570 |

*Primary Examiner*—Thurman K. Page
*Attorney, Agent, or Firm*—John W. Routh

[57] ABSTRACT

A pharmaceutical dosage form is provided which disintegrates rapidly in water having an open matrix network structure comprised of mannitol and a natural gum and which can be used particularly for oral administration to pediatric and geriatric patients.

3 Claims, No Drawings

FAST DISSOLVING DOSAGE FORMS

This invention relates to fast dissolving dosage forms for oral administration containing a chemical, such as a pharmaceutical, substance and which dissolve, for example, in the mouth within 10 seconds. More particularly, this invention relates to an improvement in such dosage forms wherein the open matrix structure comprises mainly mannitol.

Backqround of The Invention

Fast dissolving dosage forms are known in the art and are desribed in U.S. Letters Pat. No. 4,371,516 issued Feb. 1, 1983. The dosage forms are described as providing a shaped article carrying a chemical, the article being capable of being rapidly disintegrated by water and comprising an open matrix network carrying the chemical, the open matrix network being comprised of a water-soluble or water-dispersible carrier material that is inert towards the chemical. The carrier material described as being particularly advantageous is gelatin which has been partially hydrolysed by heating a solution of gelatin in water e.g. in an autoclave at about 120° C. for from about 5–60 minutes. The patent discloses that other carrier materials may be used for example polysaccharides such as hydrolysed dextran, dextrin and alginates or mixtures with each other or with other carrier materials such as polyvinyl alcohol, polyvinylpyrrolidine of acacia. Since this invention relates to an improvement in sucn shaped articles, the disclosure of U.S. Pat. No. 4,371,516 is incorporated into this application by reference in its entirety. The improvement provided by the high mannitol content is improved stability of the dosage form in a blister pack at high humidity levels.

Summary of The Invention

This invention is an improved pharmaceutical dosage form for oral administration as a solid, which dosage form can be disintegrated by water within ten seconds and which consists essentially of an open matrix network carrying a unit dosage of a pharmaceutical substance, the open matrix network consisting essentially of a pharmacologically acceptable water-soluble or water-dispersible carrier material, and the improvement comprising selecting the carrier material from the group consisting essentially of mannitol in admixture with a natural gum, preferably acacia, guar gum, xanthan gum and tragacanth gum. Other suitable natural gums include locust bean gum, pectin, algin, agar, carrageenan and gum arabic. Preferably the mannitol constitutes at least about 10% by weight of the final dosing suspension and no more than about 15% by weight.

Detailed Description of The Invention

The improved pharmaceutical dosage forms of the invention and their preparation are illustrated by the following examples.

Example 1

In this example, the pharmaceutical substance is chlorpheniramine maleate and the natural gum component is a mixture of guar gum and acacia gum. The formulation for the dosage form is as follows:

| Ingredient | Quantity % w/w |
|---|---|
| Chlorpheniramine Maleate, USP | 0.80 |
| Colloidal Silicon Dioxide, NF | 0.40 |
| Mannitol, Granular, USP | 15.00 |
| Starch, Pre-gelatinized | 1.00 |
| Guar Gum, MM | 0.20 |
| Acacia Gum, NF | 3.00 |
| Nutrasweet, NF | 0.40 |
| Propylparaben, NF | 0.025 |
| Nat. Peppermint Flavor 410449 | 0.10 |
| Methylparaben, NF | 0.075 |
| Deionized Water, USP | 79.0 |

The procedure for preparing a batch of suspension was stepwise as follows:

The deionized water was divided in a one-third portion, designated portion A, and a two-thirds portion, portion B. Portion A was heated to 75° C. and the methylparaben and propyparaben were added slowly with stirring until dissolved. Separately the colloidal silicon dioxide was added to portion B and stirred until evenly dispersed. Portion A was then added to portion B. The temperature of the mixture rose to 30–40° C. Then added separately with stirring until dissolved were mannitol grannules, the pregelatinized starch, Nutrasweet, chlorpheniramine maleate, acacia gum, and guar gum.

The freeze drier employed in this example was a Virtis 25 SRC Model Freeze Drier. The fast dissolving dosage forms were prepared by dosing 500 milligrams of the suspension into each well in a thermoformed blister tray containing 10 wells per tray. The filled trays were placed in a larger tray containing a dry ice-methanol mixture. When the suspension in the wells were frozen, the samples were placed on the freeze dryer trays at a shelf temperature of −45° C. When the samples had reached a temperature of −45° C., as determined by a probe in a well, the condenser was turned on and the freezer turned off. The condenser temperature was brought to between −40 and −45° C. and the vacuum was turned on to between 50 and 60 millitorrs. The heater was then turned on and the shelf temperature was adjusted to 50–55° C. The heat-dry cycle lasted for 3 hours. The vacuum, the condenser and the heater were turned off and the samples removed. The wafers from each batch were removed from the wells in the trays. They were white in color and each weighed about 105 milligrams of which about 40 milligrams was chlorpheniramine. The wafers were crisp, when placed on the tongue exhibited a good flavor and disintegrated rapidly. When placed in water at 37° C., the wafers dissolved in less than 10 seconds.

EXAMPLE 2

In this example, two batches, were prepared which differed only in the weight percents of mannitol and water, the mannitol being 12.5% w/w in the first and 15% w/w in the second. Each formulation produced wafers that were crisp and exhibited a good snap and good dissolution time, each dissolving in water at 37 ° C. in less than 10 seconds. The formulations are presented below and the procedure for their preparation is essentially the same as described in Example 1 above except that the batch having 12.5% mannitol had to be deaerated because it was foamy.

| Ingredient | Quantity % w/w | Quantity % w/w |
|---|---|---|
| Chlorpheniramine Maleate, USP | 0.80 | 0.80 |
| Colloidal Silicon Dioxide, NF | 0.40 | 0.40 |
| Mannitol, Granular, USP | 12.50 | 15.00 |
| Methylparaben, NF | 0.075 | 0.075 |
| Prepylparaben, NF | 0.025 | 0.025 |
| Nat. Peppermint Flavor 410449 | 0.10 | 0.10 |
| Nutrasweet, NF | 0.40 | 0.40 |
| Xanthan Gum, NF | 0.10 | 0.10 |
| Guar Gum, MM | 0.10 | 0.10 |
| Tragacanth Gum, NF | 0.50 | 0.50 |
| Deionized Water, USP | 85.0 | 82.5 |
| | 100 | 100 |

EXAMPLE 3

In this example, in addition to chlorpheniramine, a second medication, phenylephrine, is added to the formulation. The wafers had good body (snap/crispness) and the disintegration time was less than 10 seconds in water at 37° C. The formulation is presented below and the procedure for its preparation is essentially the same as described in Example 1.

| Ingredient | Quantity % w/w |
|---|---|
| Chlorpheniramine Maleate, USP | 0.80 |
| Phenylephrine Hydrochloride, USP | 2.00 |
| Mannitol, Granular, USP | 15.00 |
| Xanthan Gum, NF | 0.10 |
| Guar Gum, MM | 0.10 |
| Tragacanth Gum, NF | 0.50 |
| Colloidal Silicon Dioxide, NF | 0.40 |
| Methylparaben, NF | 0.075 |
| Propylparaben, NF | 0.025 |
| Nutrasweet, NF | 0.4 |
| Nat. Peppermint Flavor, 410449 | 0.1 |
| Deionized Water, USP | 80.5 |

Although we do not intend to be bound by any theory of the invention, it is believed that the mannitol and the gum provide the structure of the wafer, the gum serving as a binding agent, and the starch serves as a wicking agent to aid in dissolution.

The amount of mannitol can vary from about 10% to about 16% by weight of the precursor liquid formulation. Amounts as high as 17.5% and 20% by weight have been tried but appear to serve no useful purpose, the increased mannitol content improving firmness but decreasing the disintegration time. The about 10% to about 16% by weight of the precursor liquid formulation calculates to about 50% to about 86% of the solid wafer dosage form. The amount of gum can vary from 0.7 to 3.2% by weight of the formulation depending upon the type of gum used.

The dosage forms of the invention advantageously are prepared in a thermoformed blister tray which is sealed with an aluminum foil cover after the freeze-drying procedure.

We claim:

1. In a pharmaceutical dosage form for oral administration as a solid, whicih dosage form can be disintegrated by water within ten seconds and which consists essentially of an open matrix network carrying a unit dosage of a water soluble pharmaceutical substance, the open matric network consisting essentially of a pharmacologically accceptable water-soluble or water-dispersible carrier material, the improvement which comprises selecting the carrier material from the group consisting essentially of mannitol in admixture with at least one natural gum, the mannitol content of the solid dosage form constituting at least abouty 50% by weight of the solid dosage form.

2. The pharmaceutical dosage from of claim 1 wherein the natural gum is selected from the group consisting of acacia gum, guar gum, xanthan gum and tragacanth gum.

3. The pharmaceutical dosage form of claim 2 wherein the natural gum content of the solid dosage form is about 0.07% to 3.2% weight.

* * * * *